(12) United States Patent
Euting et al.

(10) Patent No.: US 9,416,399 B2
(45) Date of Patent: Aug. 16, 2016

(54) METHOD FOR PURIFICATION OF NUCLEIC ACIDS, PARTICULARLY FROM FIXED TISSUE

(71) Applicant: Siemens Healthcare Diagnostics Inc., Tarrytown, NY (US)

(72) Inventors: Heike Euting, Bocholt (DE); Guido Hennig, Köln (DE); Alexandre Izmailov, Toronto (CA)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 62 days.

(21) Appl. No.: 14/199,019

(22) Filed: Mar. 6, 2014

(65) Prior Publication Data

US 2014/0186236 A1    Jul. 3, 2014

Related U.S. Application Data

(62) Division of application No. 13/133,182, filed as application No. PCT/EP2009/065534 on Nov. 20, 2009, now Pat. No. 8,703,931.

(30) Foreign Application Priority Data

Dec. 12, 2008    (DE) .................. 10 2008 061 714

(51) Int. Cl.
  *G01N 33/553*    (2006.01)
  *C12Q 1/68*    (2006.01)
  *C07B 63/00*    (2006.01)
  *C12N 15/10*    (2006.01)

(52) U.S. Cl.
  CPC .............. *C12Q 1/6806* (2013.01); *C07B 63/00* (2013.01); *C12N 15/1013* (2013.01); *Y10T 137/8376* (2015.04)

(58) Field of Classification Search
  None
  See application file for complete search history.

(56) References Cited

U.S. PATENT DOCUMENTS

| | | | |
|---|---|---|---|
| 5,346,994 A | 9/1994 | Chomczynski | |
| 5,897,783 A * | 4/1999 | Howe et al. | .............. 210/695 |
| 6,090,546 A | 7/2000 | Breivik et al. | |
| 6,194,562 B1 | 2/2001 | Smith et al. | |
| 6,787,307 B1 | 9/2004 | Bitner et al. | |
| 2006/0240448 A1 | 10/2006 | Bitner et al. | |

FOREIGN PATENT DOCUMENTS

| | | |
|---|---|---|
| EP | 0819696 | 1/1998 |
| EP | 1468430 | 7/2003 |
| EP | 1510577 | 3/2005 |
| WO | 9014891 | 12/1990 |
| WO | 0146402 | 6/2001 |
| WO | 03040364 | 5/2003 |
| WO | 03058649 | 7/2003 |
| WO | 2005021748 | 3/2005 |
| WO | 2006071770 | 7/2006 |
| WO | 20090153299 | 12/2009 |

OTHER PUBLICATIONS

Beckman Coulter; "Agencourt FormaPure KIT, Nucleic Acid Isolation from Formalin-Fixed, Paraffin-Embedded Tissue", URL: https://www.beckmancoulter.com/wsrportal/biblography?docname=Protoco1000385v005.pdf; downloaded Nov. 13, 2013.

Ambion—The RNA Company: "96 well Magnetic-Ring Stand", Jun. 18, 2008, (XP002570156, gefunden im Internet: URL: http://www.ambion.com/techlib/spec/sp_10050.pdf).

Ambion: "High Throughput RNA Recovery from Mammalian, Plant and Viral Samples", Ambion TechNotes Newsletter, 13(1): 24-25 (2006).

Berensmeier Sonja: "Magnetic particles for the separation and purification of nucleic acids," Applied Microbiology and Biotechnology, 73(3): 495-504 (2006).

Gilbert M T P et al, "The Isolation of Nucleic Acids from fixed, paraffin-embedded Tissues—which Methods are useful when", PLoS One, Public Library of Science, 2(6): E537 (2007).

Fang X., et al., High-Throughout Sample Preparation from Whole Blood for Gene Expression Analysis, J. of the Association for Laboratory Automation, 11(6):381-386 (2006).

International Search Report for WO 2010/066554, Mar. 24, 2010.

Siemens, Brochure: "True molecular testing versatility to meet your laboratory Needs. The VERSANT kPCR Molecular System," (2008).

Gaillard, Claire et al., Avoiding adsorption of DNA to polypropylene tubes . . . , Technical Tips Online, 3: 63-65, (1998).

Gleizes, A. et al. Brochure: "Automation of the INVITROGEN ChargeSwitch® Forensic DNA Purification kit for Genotyping from forensic samples," Life Science Robotics, (2006).

Zechenbauer, Ulrike, "How to Fingerprint a Tumor" Pictures of the Future, pp. 100-102, (2008).

Anonymous, from magnet-shop.net; "Ringmagnet ∅ 20,0×6,4×5,0 mm N35H Nickel m. Senkung Süd," (2016).

* cited by examiner

*Primary Examiner* — Patrick Lewis

(57)    ABSTRACT

The invention relates to a method for purification of nucleic acids, to a kit for performing the method according to the invention and to a new application of magnetic particles for purification of a biological sample. The method according to the invention comprises the following steps: a) accommodating of the sample in a first sample vessel in an aqueous solution and lysing of the sample under non-chaotropic conditions; suspending of first magnetic particles in the solution and inserting of the first sample vessel in a sample vessel holder, wherein the sample vessel is inserted in the annular interior space of a ring magnet associated with the sample vessel holder; separating of the solution from the magnetic particles; and isolating of the nucleic acids from the solution.

10 Claims, 2 Drawing Sheets

METHOD FOR PURIFICATION OF NUCLEIC ACIDS, PARTICULARLY FROM FIXED TISSUE

This application is a divisional of U.S. application Ser. No. 13/133,182 which was filed on Jun. 7, 2011 which is the US National Stage of International Application No. PCT/EP2009/065534 filed Nov. 20, 2009. The International Application claims the benefit of German Patent Office Application No. 102008061714.8 filed Dec. 12, 2008. All of the applications are incorporated by reference herein in their entirety.

The invention relates to a method for purifying nucleic acids, to a system for carrying out the method according to the invention, and also to a sample vessel holder for the purification of a biological sample.

Molecular diagnostics has recently become increasingly important. It has found a way into the clinical diagnosis of diseases (inter alia, detection of infectious agents, detection of mutations of the genome, discovery of circulating tumor cells, and identification of risk factors for the predisposition to a disease). But also in veterinary medicine, environmental analysis, and food testing, use is meanwhile being made of molecular diagnostics methods. Tests at pathology/cytology institutes or in the context of forensic problems represent a further area of application. But also in the context of healthcare (e.g., tests on blood supplies for absence of infectious agents), use is meanwhile being made of gene diagnostics, and lawmakers are planning to regulate such tests by law in the future. Methods which are also used in clinical molecular diagnostics (such as, for example, hybridization or amplification techniques, such as the polymerase chain reaction (PCR), transcription-mediated amplification (TMA), ligase chain reaction (LCR), branched DNA (bDNA) or nucleic acid sequence-based amplification (NASBA) technologies) are also part of the routine procedures in basic scientific research.

In particular, nucleic acid analysis opens promising new possibilities in the research and diagnosis of cancers, by determining gene expression in tissues. Thus, for example, microarray systems have opened the possibility of determining the expression of hundreds or even thousands of genes in a single reaction. The sample material, purified nucleic acids, for example RNA or cDNA, is applied to a chip which comprises corresponding capture oligonucleotides, and so the nucleic acids in the sample can be detected by hybridization. In addition, other methods for detecting nucleic acids in a sample, for example amplification methods such as the polymerase chain reaction (PCR), are also widespread.

A fundamental problem in nucleic acid analysis is sample preparation. The sample to be investigated usually comprises cells or tissue with interfering, partially insoluble constituents (known as debris) which can interfere with the subsequent isolation and analysis. Such insoluble constituents occur particularly in the case of nucleic acid isolation from stool/feces, blood, warts, calcified structures (bones), or else heavily necrotic tissue samples. However, debris can, in the broadest sense, also include soluble components, for example released hemoglobin from erythrocytes which is present in a great excess and will be removed during the isolation of the nucleic acids.

This problem is particularly serious in tumor diagnostics because use is often made here of formalin-fixed, paraffin-embedded (FFPE) sections as sample material. When taking samples from patients, for example during biopsies or when taking intraoperative samples of tumor material, tissue material is fixed with formalin and embedded in paraffin in order to preserve the sample material. During the incubation—but also still for years thereafter in the tissue block—the fixatives result in extreme crosslinking of biomolecules (nucleic acids with proteins, and proteins with one another or nucleic acids with one another). These crosslinked structures inside and outside cells contribute to the production of insoluble debris, or nonlysable or difficult-to-lyse debris. From the samples embedded in the paraffin, sections are usually made for assessment by pathologists; however, these sections can also be used as starting material in nucleic acid analysis. In this case, both cellular debris and the paraffin have to be removed during the purification of the nucleic acids after lysis.

Furthermore, this problem with interfering, partially insoluble constituents (debris) also occurs during the purification of nucleic acids from stool samples (feces, dung). Stool samples consist of not only the indigestible portions of food (fiber) but also undigested remnants, such as fat, starch, connective tissue fibers and muscle fibers, and water, which were not absorbed in the upper sections of the large intestine. Endogenous substances present include: shed intestinal cells, residues of digestive enzymes and mucus. Moreover, low amounts of the bile acids themselves, and also of the lecithin likewise discharged from the gall bladder to protect the intestinal mucosa, and of other phospholipids are discharged along with the dung.

In order to lower costs and to keep the processing time from sample input until determination of the analytical result as short as possible, an overriding goal is to make methods for purifying nucleic acids as efficient as possible and to carry out the methods by automated means as far as possible. This is the case particularly in diagnostics. Highly suitable for automation are those methods which can be carried out in very few different reaction vessels and can be carried out in standardized formats (e.g., 96-well plate format), because efficient pipetting robots can be used in this method. Therefore, there is the need in the prior art for simple, efficient, and highly automatable sample preparation.

Customary methods for nucleic acid purification comprise sample lysis under chaotropic conditions, purification by extraction, precipitation and purification from the liquid phase, for example phenol-chloroform extraction (see Sambrook et al., Molecular cloning—a laboratory manual, 3rd edition, Cold Spring Harbor Laboratory, Cold Spring Harbor Press, 2001, ISBN-13: 978-0879695774), or column-based purification methods, as disclosed in WO 2003040364-A1 for example.

A customary method for isolating nucleic acids has been described by Chomczynski (U.S. Pat. No. 5,346,994) and comprises the purification of nucleic acids from tissue material based on separation from the liquid phase using phenol and the chaotropic compound guanidine isothiocyanate. The sample has to be homogenized in an aqueous solution and, after addition of guanidine isothiocyanate (GTC) and phenol/chloroform, centrifuged. Proteins are found in the organic phase, DNA is found in the interphase, and RNA is found in the aqueous phase. The RNA can be precipitated from the aqueous phase. However, this method does not enable reliable purification of RNA from FFPE tissue samples.

Other known methods for DNA or RNA isolation typically use chaotropic salts or phenol extraction.

EP0819696 discloses a method for purifying nucleic acids which is based on the binding of nucleic acids to silica or other silicon dioxide derivatives under chaotropic conditions. The sample is lysed in a chaotropic lysis buffer and the nucleic acids are bound to a silica matrix.

Methods known in the prior art for purifying nucleic acids from paraffin sections initially require laborious deparaffinization, where the paraffin is typically removed by xylene, and laborious subsequent rehydration with a xylene/ethanol dilution series.

For instance, WO 200146402 A1 describes a method for purifying RNA from fixed paraffin sections in which the paraffin section is initially placed into an Eppendorf reaction vessel and deparaffinized with xylene. Subsequently, the section has to be rehydrated with a xylene/ethanol dilution series. Subsequently, the sample is heated in a chaotropic solution over a prolonged period (5 to 120 minutes) to purify the RNA. Although this method enables effective deparaffinization, it is laborious and, owing to the need for multiple centrifugation steps, not very suitable for automation.

EP1510577 furthermore discloses a method in which nucleic acids bind to magnetic particles under chaotropic conditions and can be separated from the sample supernatant by applying a magnetic field. WO1990014891A1 discloses a magnetic sample holder which can be used for this purpose. However, in this method, there is no prior purification of the sample from cellular debris or deparaffinization under nonchaotropic conditions. The presence of debris in the sample in the purification of nucleic acids has, however, a disadvantageous effect and is disadvantageous particularly in automated methods because the debris can clog pipette tips, suction lines, and the like, and can damage pressure sensors which are used to monitor the pipetting step.

With respect to the prior art, there is therefore a need for improved methods for purifying nucleic acids and, in particular, for methods which are suitable for automation.

Definitions

The expression "biological sample" refers to any sample which comprises cells or cellular material, in particular cells, frozen cell pellets, fixed cells, feces/stool, buffy coat (=white blood cell fraction of blood), ascites, swabs, in particular cheek or throat swabs, but very preferably cervical swabs, sputum, organ punctates, sperm, tissue samples, fixed tissue samples, tissue sections of fixed or nonfixed tissue samples, in particular frozen sections and paraffin sections, in particular formalin-fixed paraffin sections, tumor material, biopsy samples, blood samples, in particular whole blood or blood fractions, cell suspensions, and in the broadest sense all samples which comprise cellular constituents, wherein both intact cells and cell constituents shall be comprised.

Furthermore, the expression "biological sample" also comprises other nucleic acid-containing, biological materials, such as, for example, blood serum or blood plasma, in particular virus-containing serum or plasma, very preferably HIV- and HCV-infected serum samples, secretions, CSF, bile, lymph fluid, urine. Similarly, it can be nucleic acid-containing materials which originate from biochemical or biotechnological processes and are to be subsequently purified.

The term "cellular" refers to both prokaryotic cells and eukaryotic cells.

The term "lysing the sample" comprises the breaking open of cells or cellular structures in the sample. It comprises in particular mechanical lysis methods (e.g., ultrasound), thermal lysis (e.g., freeze-thaw cycles, heating the sample), and chemical lysis (e.g., with detergents). However, the expression "lysing the sample" is not restricted to cells and can also refer to the release of nucleic acids by the described methods from noncellular, biological structures or complexes.

The expression "nucleic acids" comprises oligomeric and polymeric ribonucleotides or 2'-deoxyribonucleotides having a chain length of more than 10 monomer units. The monomer units in nucleic acids are linked via phosphodiester bonds between the 3' and 5' hydroxyl groups of adjacent monomer units, and a heterocyclic base is glycosidically bonded to the 1' atom of the respective carbohydrate component. Nucleic acids can form double and triple strands by forming intermolecular hydrogen bonds. The meaning also includes protein/nucleic acid complexes and also nucleic acids with synthetic nucleotides, such as morpholinos, LNAs, or PNAs.

The term "chaotropic conditions" refers to solvent conditions in the presence of chaotropic agents or compounds. Chaotropic agents or compounds are compounds which change or disrupt the secondary structure, tertiary structure, and quaternary structure of proteins, nucleic acids, and protein-nucleic acid complexes while the primary structure remains intact. In solution, under chaotropic conditions, the intramolecular interactions of biological molecules, in particular proteins, protein-nucleic acid complexes, and nucleic acids, are disrupted, since chaotropic compounds interfere with stabilizing intramolecular interactions in biological molecules, for example hydrogen bonds, van der Waals forces, and hydrophobic effects. Chaotropic compounds usually have large-volume ions which, owing to their size, can interfere with the intramolecular interactions and reduce the polarity of the solvent as a result, thereby disrupting intermolecular and intramolecular hydrogen bonds. Consequently, many proteins precipitate; however, the helical structure of double-stranded nucleic acid segments is maintained. By adding chaotropic compounds to cell lysates or cell suspensions, proteins can be precipitated while nucleic acids remain in solution. Under chaotropic conditions, the binding of nucleic acids to silicon dioxide-based matrices is greatly favored. Chaotropic compounds comprise, for example, high molecular weight urea solutions (e.g., 6 to 8 mol/l urea), guanidinium salt solutions (e.g., 6 mol/l guanidinium chloride), high molecular weight lithium salts (e.g., 4.5 mol/l lithium perchlorate). Chaotropic anions comprise the anions $F^-$, $PO_4^{3-}$, $SO_4^{2-}$, $CH_3COO^-$, $Cl^-$, and in particular $Br^-$, $I^-$, $NO_3^-$, $ClO_4^-$, $SCN^-$, and $Cl_3CCOO^-$. Chaotropic cations comprise the cations $Li^+$, $Mg^{2+}$, $Ca^{2+}$, $Ba^{2+}$, and in particular the guanidinium cation $[CH_6N_3]^+$. Chaotropic compounds preferred for nucleic acid isolation are guanidinium isothiocyanate ($[CH_6N_3]^+$ $SCN^-$) and guanidinium chloride.

The term "nonchaotropic conditions" refers to solvent conditions in an aqueous and/or alcoholic solution in the absence of chaotropic agents.

The term "purifying nucleic acids" describes the incomplete or complete removal of non-nucleic acid constituents from a nucleic acid-containing sample. It is not restricted to the attainment of a particular degree of purity.

The term "automated purification" comprises methods which entirely, or else only in partial steps, replace the manual labor of human personnel and are used in particular in the steps of disrupting the bodily biological sample with a specific buffer, of adding magnetic particles or alternative binding methods, of incubating at a particular temperature, of removing nonabsorbed sample constituents; in the wash steps; in the elution of bound nucleic acids from a solid-phase matrix, for example from magnetic particles at a particular temperature; and in the separation of the eluate from the particle suspension.

The term "separation" comprises removing as far as possible all biological or chemical substances or components which are not the actual target of the isolation—i.e., which essentially are not nucleic acids. In particular, the separation of these substances serves to avoid interference or disturbances during the actual binding, enrichment, purification, and subsequent detection of the target molecules.

The term "cellular debris" comprises all biological components which are not the primary target of nucleic acid isolation and are to be separated from the actual target molecules by a purification or negative selection step. After lysis of a cellular sample, this includes cell constituents which are insoluble and difficult to lyse, particularly in an aqueous solution, such as, for example, necrotizing tissue constituents, bone or lime structures, in particular microcalcifications, but also as well burst or morphologically altered erythrocytes, wart-like and papilloma-like tissue structures, and also specific bacteria which have a complex, difficult-to-lyse sugar coat (e.g., mycobacteria). Moreover, this includes proteins, membrane constituents, structures crosslinked particularly due to fixing, etc. In individual cases, it can, however, also be water-soluble components which are released according to the above-described lysis processes and are to be separated. An example is the hemoglobin which is released in large amounts and in a molar excess with respect to nucleic acids, after the lysis (e.g., by means of hypotonic buffer conditions) of erythrocytes, and which is to be separated prior to further processing of the bodily sample. Furthermore, "cellular debris" means in particular all components in feces/stool which are not nucleic acids. Stool consists of not only the indigestible portions of food (fiber) but also undigested remnants, such as fat, starch, connective tissue fibers and muscle fibers, and water, which were not absorbed in the upper sections of the large intestine. Endogenous substances present include: shed intestinal cells containing nucleic acids which are to be isolated, residues of digestive enzymes and mucus. Moreover, low amounts of the bile acids themselves, and also of the lecithin likewise discharged from the gall bladder to protect the intestinal mucosa, and of other phospholipids are discharged along with the dung.

The term "magnetic particles" comprises both organic and inorganic magnetic particles.

The term "silica" comprises silicon dioxide and silicon dioxide derivatives, in particular $SiO_2$ crystals and other forms of $SiO_2$, for example diatoms composed of $SiO_2$, zeolites, amorphous silicon dioxide, glass powder, silicic acid, waterglass, and also aluminum silicates and activated silicates.

The term "hydrophobic matrix" refers to a solid phase, the surface of which is made of a hydrophobic material, in particular a hydrophobic plastic material, for example polyolefins, such as polypropylene (PP), polyethylene (PE), halogenated polyolefins, such as, for example, PTFE (polytetrafluoroethylene), and others. The matrix may be present in any suitable form, for example in the form of particles, fibers, flat surfaces, etc. In particular, the matrix may be in the form of an inner vessel wall.

The term "lysis buffer system" includes a buffer system which comprises at least one substance which is able to cause or favor the disruption of a cell, a cell system, cell constituents, or other biological complexes or structures. The substances are especially often selected from the group of detergents (Triton X-100, SDS, or the like) and enzymatic reagents, such as proteinase K in particular. Also comprised is the use of reagents from the group of aqueous, buffered or unbuffered solutions (water in the simplest case). In a lysis buffer system, one or more components may be combined from one or both groups or with one another. In the context of this invention, reagents which comprise chaotropic substances expressly do not mean a constituent of the lysis buffer system in the first steps of a purification.

The other terms used in the present application have the usual meaning known to a person skilled in the art.

SUMMARY OF THE INVENTION

The invention relates to a method for purifying nucleic acids from a biological sample, comprising the following steps:

a) collecting the sample in a first sample vessel in an aqueous solution and lysing the sample under nonchaotropic conditions;
b) suspending first magnetic particles in the solution;
c) placing the first sample vessel into a sample vessel holder, wherein the sample vessel is placed into the annular interior space of a ring magnet associated with the sample vessel holder;
d) separating the solution from the magnetic particles; and
e) isolating the nucleic acids from the solution.

The invention further relates to an automated system for carrying out the method and to a sample vessel holder for carrying out the method.

The invention is based on the finding that cellular debris can be removed very effectively from the solution by the magnetic particles. The use has multiple advantages: because the sample vessel is accommodated in the annular interior space of the magnet, it is additionally stabilized in the holder. The magnetic forces have a uniform effect on the magnetic particles, and an annular, fringe-like deposit of the magnetic particles and of the cellular debris forms on the wall of the sample vessel. The bulge which is caused by an annular deposit of the particles is especially small, and the debris is deposited on the wall of the sample vessel with an annular distribution, making it possible for the liquid sample to be effectively withdrawn, for example by using a pipetting apparatus, while the risk of contamination owing to contact of the pipette tip with the deposit is minimized. More specifically the formation by the deposits of magnetic particle structures which emanate in a hedgehog-like or spiky manner—as is observed in particular in the case of rod magnets with a magnetic field aligned in one orientation—is avoided. Therefore, this method is suitable in particular for automated procedures.

In particular, the use of a ring magnet offers the following further advantages:

Ring magnets having a field orientation which is parallel to the axis of symmetry of the ring achieve the most compact particle deposit without the formation of thread-like structures along the field lines, as is observed in the case of rod magnets (known as "hedgehog structures").

Ring magnets minimize any incorrect positioning of the sample vessels in automated pipetting systems (known as pipetting robots) and hence misalignment of automated pipetting apparatuses.

Ring magnets minimize the risk of particle loss or contaminations in pipetting robots.

The invention is similarly based on the finding that the sample vessel holder having the ring magnet is capable of combining various functional steps of an automated purification in one material unit: a) sample identification by reading bar codes on the sample vessel in the sample vessel holder; b) the addition of reagents, such as lysis buffer and/or proteinase K for example, and magnetic particles; c) after lysis and the addition of magnetic particles, the removal of debris in the sample vessel by magnetization in the ring magnet in the sample vessel holder. Here, the method according to the invention is characterized in particular by there being no need for aspiration of liquids by robot tips in any of steps a-c. Aspiration and the associated transfer of liquids into secondary sample vessels is carried out only after the removal of debris or interfering components by the magnetic particles under nonchaotropic conditions.

According to one aspect of the invention, the magnetic particles have a mean size of <50 µm, preferably <10 µm, very preferably <0.5 µm, not excluding <0.1 µm, wherein the size is determined by transmission electron microscopy methods.

According to one aspect of the invention, these particles have a silicon-containing coating, in particular a silicon dioxide-comprising coating. Such magnetic particles are, for example, known from EP 1468430, herein incorporated by reference.

The magnetic particles preferably have a silica coating, i.e., are $SiO_2$-coated magnetic particles. The expression "$SiO_2$-coated magnetic particles" comprises magnetite cores which consist of at least 90% by weight of $Fe_3O_4$ and the surface thereof is coated with silicate.

The magnetic particles are suspendable particles which, by application of an external magnetic field, can be immobilized in the magnetic field.

The magnetic particles are separated from the solution after immobilization of the particles by the magnetic field; the solution can then be separated from the particles in any suitable manner, for example by decanting, aspiration, etc.

The isolation of the nucleic acids from the sample according to step (e) can be carried out with any suitable method, for example extraction methods, column-based methods, precipitation, etc. Step (e), isolating nucleic acids, is not restricted to any particular degree of purity of the isolated nucleic acids.

In step (a), the sample is collected in an aqueous solution. This can be effected by mixing, suspension, emulsification, or dissolution. The sample can be mechanically reduced in size before or after collection in an aqueous solution, for example by mechanical action (e.g., cutting, stirring), by the action of heat, by ultrasound treatment and similar methods. However, it is also possible to suspend the intact tissue sample, for example a tissue section, directly in an aqueous solution.

According to one aspect of the invention, the sample is a blood sample. In the case of complete blood lysis, hemoglobin and also erythrocyte and leukocyte membrane constituents are released, in large amounts and in a molar excess with respect to the nucleic acids, and can be separated in step d). Step e) is then used for specific purification of the nucleic acids from the aqueous residual phase.

Alternatively, it is possible, as already described technically, to carry out selective lysis of erythrocytes under, for example, hypotonic buffer conditions. This releases hemoglobin and erythrocyte membranes in large amounts, and they can be separated in step d). In this case, the leukocyte lysis, which is still required, with release of the nucleic acids would be carried out in step e) upon addition of a chaotropic buffer and possibly proteinase K. This procedure enables simple and complete automation of the extraction of nucleic acids from blood, in particular leukocytes, and makes it possible to avoid laborious procedural steps, such as centrifuging and pelleting the leukocytes and discarding the supernatant.

According to a further aspect of the invention, the sample is a stool/feces sample. The lysis of stool releases nucleic acids from healthy or pathologically altered, discharged intestinal epithelial cells into a complex matrix of cell remains, fiber, undigested food residuals, such as fat, starch, connective tissue fibers and muscle fibers, residues of digestive enzymes and mucus, bile acids, lecithins and other phospholipids.

All components of the sample which are not nucleic acids can be completely or partially separated in step d). Step e) is then used for specific purification of the nucleic acids from the aqueous residual phase.

According to one aspect of the invention, the biological sample is a paraffin-embedded sample, in particular a paraffin section, and/or a fixed sample, in particular a formalin-fixed paraffin section.

The method according to the invention is especially suitable for the processing of fixed samples, since fixed samples comprise particularly large amounts of debris owing, for example, to protein and nucleic acid crosslinking.

According to a preferred aspect of the invention, the solution is heated prior to step (d) to at least 50° C., preferably 50-95° C., preferably at least 60° C., more preferably 60-80° C. An advantage of this heating is that it enables better suspension and improved lysis of the biological sample in the aqueous solution. For more effective lysis, a proteinase is preferably added, in particular proteinase K.

According to one aspect of the invention, the sample is cooled again to below 50° C. prior to step (d). In the case of paraffin being present in the sample, cooling to below 50° C. has the additional advantage of the paraffin solidifying again, for example in the form of a paraffin ring on the vessel wall. The sample or the lysate can then be sucked off very easily and accurately without any clogging problems using, for example, a pipette tip, with the paraffin remaining in the reaction vessel in the form of the described paraffin ring.

According to a further aspect of the invention, the sample or the lysate is contacted with a hydrophobic matrix by, for example, being collected in a vessel composed of hydrophobic plastic material. This is preferred especially when processing paraffin-containing samples. Suitable as a hydrophobic matrix for this purpose are, for example, the well-known reaction vessels from Eppendorf or Sarstedt, which consist of polyolefins (e.g., polypropylene and polyethylene). Particular preference is given to heating paraffin-containing samples in contact with a hydrophobic matrix to over 50° C. prior to step (d) because the paraffin melts as a result and advantageously settles upon cooling as a ring at the liquid surface on the matrix, for example on the vessel edge in the case of a plastic reaction vessel. This occurs owing to absorption processes of the liquefied paraffin on the hydrophobic matrix. As a result, the liquid sample can then be advantageously sucked off with accuracy in subsequent steps, without clogging of pipette tips, while the paraffin ring remains in the reaction vessel.

According to a further aspect of the invention, the purification efficiency of the described method is so high that, for most applications, it is sufficient to use a single 3-20 µm paraffin section, very particularly preferably a single 10 µm paraffin section, in order to achieve very high yields of nucleic acids. As a result, the amount of paraffin used is below critical amounts which prevent or interfere with formation of the ring.

According to one aspect of the invention, the solution in step (d) is separated from the magnetic particles by aspiration.

According to one aspect of the invention, step (e) further comprises the addition of a chaotropic compound to the solution. This may include the first-time or repeated addition of proteinase K (if proteinase K was already used in step a)) in step e), i.e., before or after the addition of the chaotropic solution.

According to one aspect of the present invention, step (e) further comprises the addition of unused (fresh) magnetic particles having a silicon-containing coating to the solution.

For the isolation of RNA, preference is given to adding a DNase in a biologically effective amount to the sample. This results in DNA being "digested" and going into solution, while the undigested RNA can be isolated from the solution. The DNase digestion can be carried out at different times during the extraction, at the earliest after lysis, and at the latest after the elution at the end of the purification.

For the purification of DNA, preference is given to adding RNase in a biologically effective amount to the sample, whereby RNA can be digested and the intact DNA can be isolated from the sample. The RNase digestion can be carried out at different times during the extraction, at the earliest after lysis, and at the latest after the elution at the end of the purification. However, preference is given to detecting the DNA in the presence of the copurified RNA, i.e., by omitting the RNase step or by using buffer conditions which enable selective isolation of DNA with exclusion of the RNA.

According to a further aspect, when placing the sample vessel into the annular interior space of the ring magnet associated with the sample vessel holder, the respective sample vessel is moved at least once out of the annular space and back in again by means of movement in the direction of the ring axis. As a result, the deposited magnetic particles together with the debris and with any paraffin residuals present are especially effectively deposited and distributed annularly on the wall of the sample vessel, further minimizing any bulge of the deposit. In contrast to conventional rod magnets having a magnetic field which acts on one side, the ring magnets prevent in particular the formation of specific, macroscopically visible spiky or hedgehog-like magnetic particle structures.

In customary methods of nucleic acid purification, the sample material is collected or lysed in a chaotropic buffer. The present invention is based on the surprising finding that nucleic acid purification gives improved results when cellular debris is removed under nonchaotropic conditions prior to the isolation of the nucleic acids from the sample. This can be achieved by, for example, centrifugation or filtration. According to one embodiment of the invention, the debris is removed with the aid of magnetic particles under nonchaotropic conditions. Preferably, these particles have a silicon-containing coating, in particular a silicon dioxide-comprising coating. Such particles are known from EP 1468430, which is incorporated herein by reference. The production of such particles is described in detail further below.

The isolation of nucleic acids from the debris-cleared lysate can be carried out by known methods. For example, extraction protocols which are based on purification from chaotropic solutions, for example by precipitation of the nucleic acids and/or absorption to silica-containing matrices under chaotropic conditions, are suitable. In the case of known column-based methods, the nucleic acids are bound to a silica membrane from the lysate in the presence of a high concentration of chaotropic salts and are eluted from the membrane after a cleaning step. Appropriate kits are commercially available from QIAGEN GmbH, Hilden, Federal Republic of Germany.

According to a preferred aspect of the invention, the isolation of the nucleic acids is carried out by renewed application of (fresh) silica-coated magnetic particles under chaotropic conditions.

According to a preferred aspect of the invention, the separation of debris or interfering substances also makes possible the increase in purification efficiency, reproducibility, and robustness, and also the reduction of outliers and ambiguous or unclear results in the analysis of the nucleic acids ("flagging" of results, "flagged" results). In clinical diagnostics, where such methods are also to be used in addition to research, this is associated with repeat tests or reflex tests, which involve additional and avoidable costs.

According to a further aspect, the invention comprises an automated system for carrying out the method according to the invention, comprising:
  a rack for at least one sample vessel;
  a temperature-controlled device having at least one slot for the sample vessel;
  a sample vessel holder for accommodating at least one sample vessel;
  a device for transporting the sample vessel holder from the rack to the temperature-controlled device;
  a device for transferring liquid from a sample vessel into, for example, a further sample vessel or a disposal apparatus (waste);
  a control for controlling the transport device, the liquid transfer device, and for controlling the temperature of the temperature-controlled device;
wherein the sample vessel holder for accommodating the at least one sample vessel comprises at least one annular magnet, in the annular interior space of which the sample vessel can be accommodated.

The invention further relates to a sample vessel holder for accommodating the at least one sample vessel, which holder comprises at least one annular magnet, in the annular interior space of which the sample vessel can be accommodated.

Preferably, the ring inner diameter of the annular magnet is, at its narrowest point, 4 to 50 mm, 4 to 20 mm, 5 to 15 mm, preferably 6 to 12 mm, in particular 8 mm.

The annular interior space can have a conical region which preferably matches the shape and geometry of a particular sample vessel.

The sample vessel holder can comprise a multiplicity of slots for sample vessels, for example 2 to 1600, preferably 2 to 96, preferably 2, 4, 6, 8, or 12. These slots can be arranged in a row or in an orthogonal matrix array, in particular 2×2, 2×3, 4×6, 6×8, 8×12, 16×24, or 32×48, as are often used in in vitro diagnostics.

Below, the invention is described with the aid of detailed examples in conjunction with the figures, in which.

Figure 1:
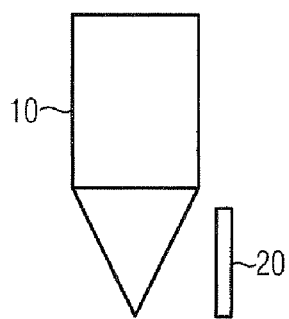
FIG. 1 shows a diagram of a sample holder with attached rod magnet having a magnetic field acting on one side according to the prior art.

FIG. 1 diagrammatically shows an arrangement of sample vessel 10 and magnet 20 according to the prior art. Such an arrangement has been disclosed by, for example, WO1990014891A1.

Figure 2:
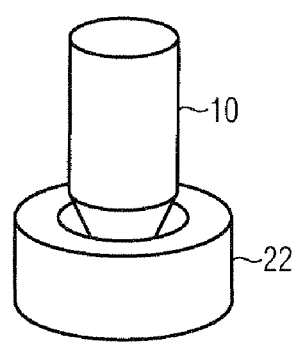
FIG. 2 shows a diagram, in top view, of a sample holder which is used in the method according to the invention.
Figure 3:
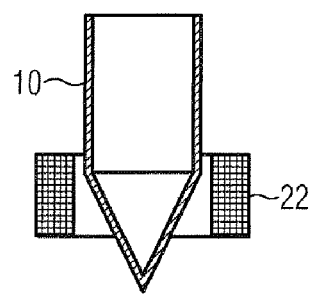
FIG. 3 shows a diagram, in cross-sectional view, of a sample holder which is used in the method according to the invention.

FIGS. 2 and 3 show the arrangement used according to the invention of sample vessel 10 and annular magnet 22. The magnet can be a ring magnet like that sold by, for example, K&J Magnetics Inc., Jamison, Pa. 18929, USA, in numerous sizes. Preferably, use is made of strong neodymium magnets, i.e., magnets which comprise neodymium-containing alloys, for example NdFeB. A ring magnet size which is especially suited to the use of the Eppendorf reaction vessels (capacity/size of 1.5-2.5 ml) that are widespread in diagnostics is an outer diameter of from 1 to 2 cm, for example 12 mm, and an inner diameter of 5-12 mm, for example 8 mm. A 1.5 ml Eppendorf reaction vessel has an outer diameter of 11 mm in the cylindrical part, and so, when using a ring magnet with an inner diameter of 8 mm, the reaction vessel can be accommodated in the annular interior space of the magnet via the conical part of the reaction vessel and can be stabilized or held thereby. Customary sample vessels have a collar at the opening, making it possible to select or to scale the magnet such that the inner diameter is smaller than the diameter of the collar but larger than the diameter of the cylindrical region below the collar of the sample vessel. In this way, the sample vessel can be held by the ring magnet.

The annular interior space can also be conical or partially conical, complementary to a conical region of the sample vessel, so that it can appropriately accommodate this vessel.

Figure 4:
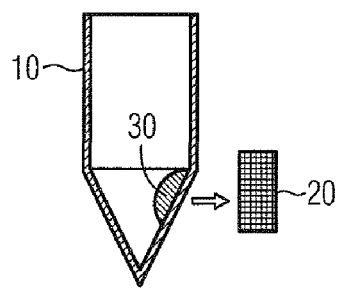
FIGS. 4 and 5 show a diagram of the different form of the deposition of particles in a sample holder according to the prior art (FIG. 4) versus a sample holder which is used in the method according to the invention (FIG. 5).
Figure 5:
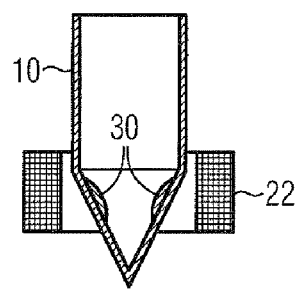

FIG. 4 shows that use of a sample holder according to the prior art leads to a strongly bulging deposit 30 of the magnetic particles, whereas use of the sample holder according to the invention results in an annular deposit with a small bulge (FIG. 5). It can be further seen that the magnetic forces here cancel each other out, whereas in the situation depicted in FIG. 4, the sample vessel is deflected by the magnet 20 in the direction of the arrow, and this is undesired particularly in automated methods, since the risk of unintended contact of the aspiration pipette (not shown) with the deposit 30 or with the sample vessel 10 increases. Furthermore, the use of the ring magnet depicted in FIG. 5 avoids in particular the formation of magnetic particle structures which emanate in a hedgehog-like or spiky manner—as is observed in particular in the case of rod magnets analogous to FIG. 4 having a magnetic field aligned in one orientation.

Figure 6:
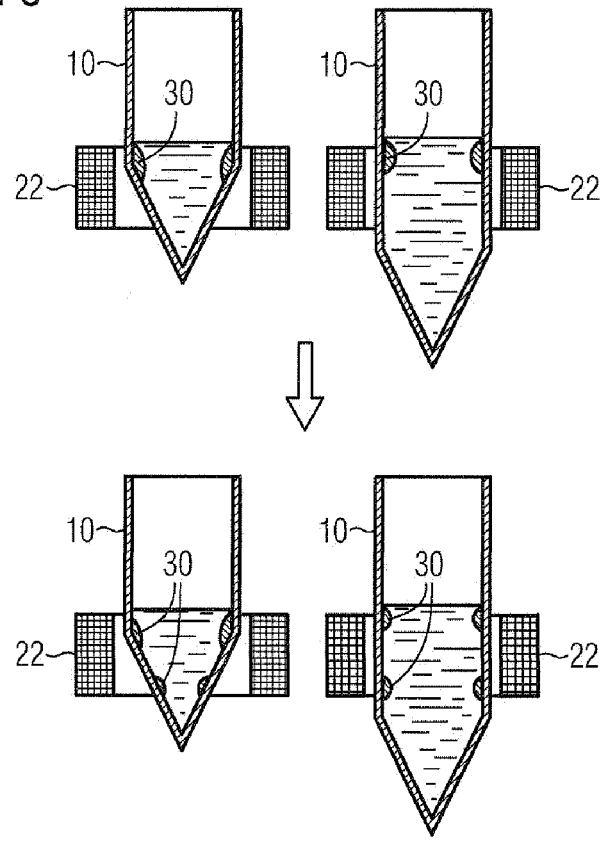
FIG. 6 shows a diagram of a development of the method according to the invention.

As shown in FIG. 6, when placing the sample vessel into the annular interior space of the ring magnet associated with the sample vessel holder, the sample vessel 10 can be moved at least once out of the ring space and back in again by means of movement in the direction of the ring axis. As a result, the deposited magnetic particles 30 together with the debris and with any paraffin residuals present are especially effectively deposited and distributed annularly on the wall of the sample vessel, further minimizing any possible bulge of the deposit. This is advantageous particularly in the case of the described purification of paraffin sections because the paraffin is then "smeared" and distributed on the vessel wall and the risk of a clogged suction apparatus is minimized.

Figure 7:
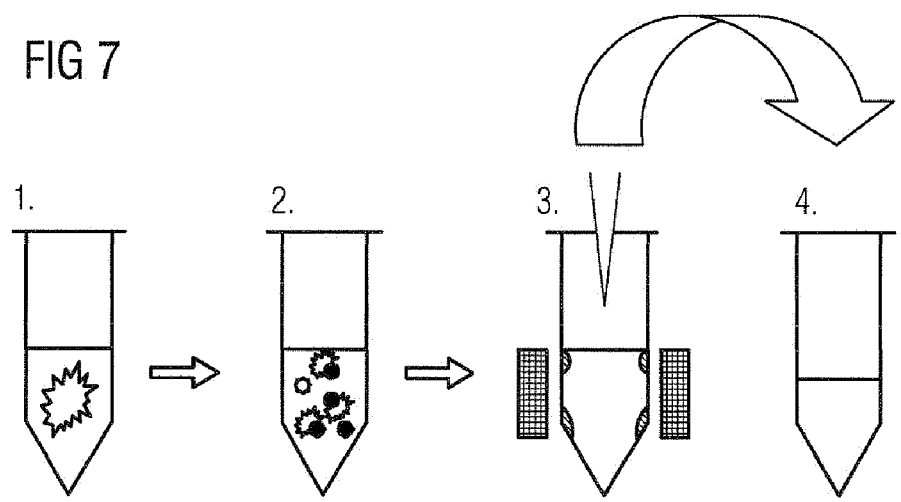
FIG. 7 shows a diagram of the method according to the invention.

FIG. 7 is a diagrammatic representation of the method according to the invention. Said method can proceed manually or in an automated manner.

EXAMPLES

Materials and Methods:

The following materials and methods were used in all of the following examples.

The starting materials are tumor samples from a clinical pathology laboratory where were fixed in formalin at the time of collection and subsequently embedded in paraffin. These methods for fixing and embedding are known in general to a person skilled in the art and are not described here in further detail. Using a microtome, tissue sections, for example having a thickness of from 5 to 10 µm, are obtained from the sample and transferred into a 1.5 ml sample vessel, for example a 1.5 ml polypropylene sample vessel (such as, for example, the well-known "Eppendorf vessel"). Alternatively, samples which have already been applied to a slide can also be detached therefrom or scraped off using a razor blade or by other suitable means (e.g., deparaffinization with ethanol/xylene) and transferred into the sample vessel.

In addition to the commercially available "Versant kPCR Sample Preparation Reagents" from Siemens Healthcare Diagnostics GmbH (Erlangen, Germany) (consisting of a proteinase K solution, binding buffer (contains chaotrope, e.g., 59% guanidine thiocyanate, and 10% octylphenoxypolyethoxyethanol), silica-coated magnetic particles, disclosed in EP 1468430 for example, wash buffer 1 (contains chaotrope or 36% guanidine thiocyanate and 30% ethanol), wash buffer 2 (contains 80% ethanol), wash buffer 3 (contains 5-chloro-2-methyl-4-isothiazolin-3-one and 2-methyl-4-isothiazolin-3-one (3:1)) and elution buffer (contains sodium azide)), the following buffers were used:

10 mM Tris-HCl
b) mM EDTA
2% SDS
pH 8.0

DNA-free DNase solution (Ambion, cat# A1906, Ambion, Foster City, Calif. 94404, USA)

Instead of the buffers of the commercially available "Versant kPCR Sample Preparation Reagents" from Siemens Healthcare Diagnostics GmbH, other customary buffer compositions known to a person skilled in the art can also be selected. Detergent-containing and/or hypotonic buffers in particular are suitable FFPE lysis buffers. Suitable wash buffers are likewise known from the prior art and commercially available. Possible binding buffers for the subsequent isolation of nucleic acids from the lysate using silica-coated magnetic beads are chaotropic buffer compositions, for example 4.5 M guanidinium HCl, 6 M guanidinium isothiocyanate, and the like. Suitable wash buffers must merely meet the requirement of ensuring that the nucleic acid is not detached from the silica matrix. In general, a high alcohol content and, optionally, a slightly alkaline pH are sufficient to prevent autoproteolysis of the DNA. Wash buffers which comprise chaotropic compounds are also suitable as long as they fulfill the abovementioned conditions. Possible elution buffers are also buffer compositions known to a person skilled in the art, for example TE buffer (10 mM Tris-HCl, 0.1 mM EDTA, pH 8.0).

It should be pointed out that, in this and similar purification protocols, the RNA can fragment into fragments which are from 100 to 500 base pairs long, but for expression analysis using established methods (RT-PCR, microarray, and the like), fragmented RNA is also well suited.

The (relative) quantification of RNA yield was achieved by means of the one-step kinetic real-time reverse transcriptase polymerase chain reaction (one-step kRT-PCR) with the aid of a TaqMan probe. For the analysis of the RNA yield, the CT value (cycle threshold, i.e., the value of the amplification cycle which is the first to exceed a defined threshold value) for the RNA of the reference or housekeeping gene RPL37A was determined, i.e., the mRNA of the human gene for ribosomal protein L37a, GenBank accession number NM_000998. The qRT-PCR was carried out using the "SuperScriptm one-step with a Platinum® Taq kit" from Invitrogen, Karlsruhe, Germany, and using primers and a probe from Eurogentec, Cologne, Germany. To carry out kRT-PCR expression analysis of RPL37A, 1 µl of purified RNA was added to 9 µl of master mix, consisting of 400 nM forward primer, 400 nM reverse primer, 200 nM TaqMan probe (FAM/TAMRA-labeled), reaction mix containing 0.2 mM of each dNTP and 1.2 mM magnesium sulfate, and also 1 µl of Platinum® Taq Mix. The reaction was carried out on an ABI7900 instrument from Applied Biosystems, Applera Deutschland GmbH, Darmstadt, Germany, with the following temperature profile:

30 min at 50° C.
2 min at 95° C.
15 s at 95° C.
30 s at 60° C., 40 cycles

To establish the CT values, the software SDS 2.0 from Applied Biosystems was used according to the operating instructions. The CT value corresponds to the number of amplification cycles above which number the amplification signal has exceeded a defined threshold, for example the measurement threshold. The more nucleic acid or RNA or DNA that is present in the sample, the lower, accordingly, is the CT value. In some cases, the CT values for RPL37A were given as 40-CT in the figures for the purpose of better presentation. In this way, the values are inverted and higher 40-CT values correspond to higher expression levels of RPL37A. Unless specified in more detail, the directly measured CT value is meant.

Example 1

Isolation of RNA from a formalin-fixed paraffin section with removal of debris by adding magnetic particles under nonchaotropic conditions This method corresponds to the method depicted diagrammatically in FIG. 7.

RNA from FFPE tissue sections was purified manually as follows:
centrifugation of FFPE tissue section in an Eppendorf sample vessel for 1 min at maximum speed;
adding 150 µl of FFPE lysis buffer and 50 µl of proteinase K;
incubation for 2 h at 65° C. with shaking (corresponds to step 1 as per FIG. 7);
adding 50 µl of magnetic particles;
mixing by shaking for 2 min (corresponds to step 2 as per FIG. 7);
placing the sample vessel into the annular interior space of the magnet, possibly further upward and downward movement of the sample vessel (corresponds to step 3 as per FIG. 7);
careful transfer of supernatant, by pipetting for example, into a new vessel (cell debris and paraffin residuals remain in the old vessel) (corresponds to step 4 as per FIG. 7).

Below, the nucleic acids can be isolated from the supernatant, for example by:
adding 800 µl of binding buffer (chaotrope);
adding 50 µl of magnetic particles;
incubating for 15 min at room temperature with shaking;
applying a magnetic field, aspirating and discarding the supernatant;
removing the magnetic field. Collecting and suspending the magnetic particles (with the bound nucleic acids) in 850 µl of wash buffer 1;
applying the magnetic field, aspirating and discarding the supernatant;
removing the magnetic field. Collecting and suspending the magnetic particles (with the bound nucleic acids) in 450 µl of wash buffer 2;
applying the magnetic field, aspirating and discarding the supernatant;
removing the magnetic field. Collecting and suspending the magnetic particles (with the bound nucleic acids) in 450 µl of wash buffer 3;
repeated washing with wash buffer 3;
after applying the magnetic field and removing the supernatant, collecting the sample in 100 µl of elution buffer, incubating for 10 min at 70° C. with shaking in a thermal mixer;
applying a magnetic field, transferring the eluate into a fresh sample vessel;
adding 10 µl of 10× DNase buffer and 1 µl of DNase I;
incubation for 30 min at 37° C.;
freezing the samples and/or further analysis of the eluate.

FIG. 7 depicts diagrammatically the method according to the invention, which can proceed manually or in an automated manner.

Example 2

Automated purification of RNA from formalin-fixed tissue sections using an additional binding step with magnetic particles to separate cellular debris Under nonchaotropic conditions RNA from formalin-fixed paraffin sections was purified using the following automated protocol on a Siemens platform, VERSANT kPCR (extraction unit). Up to 48 tissue sections can be purified in one run.

Sample Preparation

Tissue sections (5-10 µm) were pelleted by centrifugation at room temperature and placed on sample carriers of the Siemens molecular platform VERSANT kPCR, where all hardware modules (sample vessel holder with ring magnet, heater/shaker, magnets, etc.), sample vessels, buffers, and pipette tips are placed at their designated positions.

Start of Purification Program:
loading the robot with one or more sample vessels which are placed into a sample vessel holder with ring magnet;
starting the purification program;
moving the sample vessel holders into the robot space;
sample vessel identification and tracking by reading a bar code, fixed on the sample vessel, in the sample vessel holder;
adding 150 µl of lysis buffer to samples in the sample vessel in a sample vessel holder with ring magnet;
adding 50 µl of proteinase K solution;
transferring the sample vessels onto a thermal shaker and incubating for 2 hours at 65° C. with shaking;
adding 50 µl of magnetic particle suspension;
incubating for 10 min at 65° C. with shaking;
incubating for 5 min without shaking;
transfer of the sample vessels from the thermal shaker back into the sample vessel holder and placing the sample vessels into the annular interior space of the magnet, possibly further upward and downward movement of the sample vessel (corresponds to step 3 as per FIG. 7);
magnetizing the samples for 3 min;
transfer of the supernatant to a deep-well sample plate (DWP);
adding 600 µl of binding buffer (chaotrope);
adding 50 µl of magnetic particle suspension to the DWP;
incubating for 10 min at room temperature with shaking;
transfer of the DWP to magnet;
incubating for 5 min at room temperature in the magnetic field;
aspirating and discarding the supernatant;
transfer of the DWP from magnet to the thermal shaker;
adding 850 µl of wash buffer 1;
shaking for 10 s at room temperature;
transfer of the DWP to the magnet;
magnetizing for 2 min at room temperature;
aspirating and discarding the supernatant;
transfer of the DWP from the magnet to the thermal shaker;
adding 450 µl of wash buffer 2;
shaking for 10 s at room temperature;
transfer of the DWP to the magnet;
magnetizing for 2 min at room temperature;
aspirating and discarding the supernatant;
transfer of the DWP from magnet to the thermal shaker;
adding 850 µl of wash buffer 3;
shaking for 10 s at room temperature;
transfer of the DWP to the magnet;

magnetizing for 2 min at room temperature;
aspirating and discarding the supernatant;
adding 100 μl of elution buffer;
transfer of the DWP from magnet to the thermal shaker;
incubating for 10 min at 70° C. with shaking;
transfer of the DWP to the magnet;
adding 12 μl of DNase mix (10 μl of 10× DNase buffer; 2 μl of DNase 1);
transfer of the DWP from magnet to the thermal shaker (cooled down to 37° C.);
incubating for 30 min at 37° C. without shaking;
transfer of the DWP to magnet;
transferring the DNase-digested samples to 1.5 ml sample vessels;
End of Purification Program
freezing the samples and/or further analysis of the RNA yield.

It becomes apparent that purification with the removal of cellular debris according to the invention results in a significantly higher yield in comparison with samples in which the cellular debris was not removed. Yields are compared via quantitative PCR of the housekeeping gene RPL37A, with the transcript amount being given as 40-CT (CT=cycle threshold, i.e., the number of amplification cycles at which the measurement threshold of the system is exceeded). This results in an improved yield with a difference of from 3 to 5 CT values of RPL37A. This corresponds to an improvement by a factor of from 8 to 32 in the yield of the total RNA. This leads to the conclusion that, firstly, unlysed tissue or cellular debris impairs the efficient and quantitative purification of nucleic acids, particularly of RNA, and presumably interferes with the binding of nucleic acids to silica-coated magnetic particles under chaotropic conditions. It also becomes apparent that centrifugation of the lysed sample under nonchaotropic conditions to remove cellular debris can be substituted with an additional purification step with silica-coated magnetic particles under nonchaotropic conditions. This has the considerable advantage of the method thus being very much more easily automatable, since no further centrifugation steps are required.

It becomes further apparent that the additional magnetic purification step to remove debris under nonchaotropic conditions also leads to more reproducible results between the consecutive sections from a tissue sample (lower variability among different RNA preparations from the same paraffin block).

The VERSANT kPCR System from Siemens, which system includes a pipetting robot from Hamilton, enables the control of all the aspiration and dispensing steps for each individual pipetting step. The movements of liquid are recorded via pressure sensors which are present in the individual pipetting channels.

These changes in the pressure ratios during each pipetting step are recorded over time (=TADM, total aspiration and dispense monitoring). For each pipetting step, certain tolerance ranges for the change in the pressure ratios can be defined. As soon as the TADM profile is outside the defined range, it is possible to directly register that the pipetting step for a sample was not carried out properly, whether this was caused by clogging of the tips, lack of liquid, foam formation in the liquid, or other negative effects. The sample can subsequently be marked for further analyses or could also be excluded from further analysis. In clinical diagnostics, this information would in many cases lead to a reflex test or repeat test, either on the same system or an alternative method.

It becomes apparent that the removal of cell debris improves the pipettability (e.g., aspiration of the lysis liquid) and efficiency of the automated purification, since the exclusion of a sample owing to a poor TADM profile occurs less often. This distinctly lowers the number of reflex tests (the test is carried out again, which test leads to a result) in clinical diagnostics, leading to a reduction in costs.

Example 3

Purification of nucleic acids from blood samples

The method according to the invention is also particularly suitable for the purification of nucleic acids from blood samples because it enables improved removal of hemoglobin or erythrocytic fragments from the blood. According to the invention, there is firstly, under nonchaotropic conditions, the efficient removal from the sample of erythrocytes, erythrocytic fragments, and also released hemoglobin, which can all interfere with later process steps.

According to a first variant, 400 μl of lysis buffer (e.g., 10 mmol Tris-HCl, 0.1 mmol EDTA, 2% SDS, pH 8.0) are added to a blood sample (e.g., 100 μl of EDTA whole blood). Subsequently, 50 μl of a magnetic particle suspension (e.g., uncoated or silica-coated magnetic particles) are added to the sample, followed by incubation for 10 min at room temperature and separation of the particles by application of a magnetic field. From the removed sample, it is then possible, as described above, to isolate nucleic acids under chaotropic conditions.

According to a second variant, the blood sample is collected in a hypotonic lysis buffer (e.g., 25 mM Tris-HCl, pH 7.5, 10 mM KCl, 5 mM $MgCl_2$), briefly incubated to lyse the erythrocytes, and subsequently a magnetic particle suspension (e.g., uncoated or silica-coated magnetic particles) is added to the sample, followed by incubation for 10 min at room temperature and separation of the particles together with the erythrocytic fragments and the hemoglobin by application of a magnetic field. Subsequently, the leukocytes are lysed under chaotropic conditions, i.e., release of the nucleic acids and binding thereof to freshly added silica-coated magnetic particles. Proteinase K can be added optionally, either beforehand or at the same time as the chaotropic reagent.

Example 4

Production of silica-coated magnetic particles

Silica-coated magnetic particles can be produced by, for example, silica coating of magnetite particles. The magnetites used are preferably hydrophilic, commercially available iron oxides ($Fe_3O_4$) which are preferably available in a narrow particle size distribution and with a spherical morphology. Magnetite particles are commercially available; products of this kind are produced by, for example, Bayer AG under the product name BAYOXIDE E. Suitable types are available under the label BAYOXIDE E8706, E8707, E8709, and E8710. Similar products are also sold by BASF under the name "Magnetic Pigment 340" or "345". Although good results can be achieved with all the products mentioned, preference is given to the use of the type BAYOXIDE E 8707 or E 8706. This magnetic pigment has a spherical morphology with a mean particle diameter of 0.2 μm and a narrow particle size distribution (about 0.1 to 0.7 μm). As starting materials for the introduction of silicate groups, use can be made of both alkali metal silicates (sodium or potassium waterglasses) and silica sols. Suitable waterglasses, which usually have very high pH values (13-14), are offered by various companies, for example Merck or Cognis. The material to be coated, for example Bayoxide E 8707, can be added with stirring to a diluted, for example 1% strength, waterglass solution. After an incubation of about 30 minutes, the material is filtered off, washed with water, and dried. According to an exemplary protocol, 50 g of Bayoxide E 8707 are added to 1000 ml of an aqueous 0.25% strength waterglass solution (HK30; Cognis) with stirring, followed by stirring for a further 30 min at RT. The particles are filtered off, washed 5 times with water and once with ethanol, and subsequently dried for 5 hours at 80° C.

The invention claimed is:

1. An automated system comprising:
   a rack for at least one sample vessel;
   a temperature-controlled device having at least one slot for the sample vessel;
   a sample vessel holder for accommodating at least one sample vessel;
   a device for transporting the sample vessel holder from the rack to the temperature-controlled device;
   a device for transferring liquid from a sample vessel and/or into a sample vessel;
   a control for controlling the transport device, the liquid transfer device, and for controlling the temperature of the temperature-controlled device;
   wherein the sample vessel holder for accommodating the at least one sample vessel comprises at least one annular magnet, in the annular interior space of which the sample vessel is accommodated.

2. A sample vessel holder for accommodating the at least one sample vessel, comprising at least one annular magnet, in the annular interior space of which the sample vessel is accommodated.

3. The sample vessel holder as claimed in claim 2, wherein a ring inner diameter of the annular magnet is, at its narrowest point, 4 mm to 50 mm.

4. The sample vessel holder as claimed in claim 3, wherein the ring inner diameter of the annular magnet is, at its narrowest point, 4 mm to 20 mm.

5. The sample vessel holder as claimed in claim 3, wherein the ring inner diameter of the annular magnet is, at its narrowest point, 5 mm to 15 mm.

6. The sample vessel holder as claimed in claim 3, wherein the ring inner diameter of the annular magnet is, at its narrowest point, 6 mm to 12 mm.

7. The sample vessel holder as claimed in claim 3, wherein the ring inner diameter of the annular magnet is, at its narrowest point, about 8 mm.

8. The sample vessel holder as claimed in claim 3, wherein the ring inner diameter of the annular magnet is, at its narrowest point, 4 mm to 50 mm, and a ring outer diameter is 1 cm to 2 cm.

9. The sample vessel holder as claimed in claim 2, wherein the annular magnet comprises a neodymium-containing alloy.

10. The sample vessel holder as claimed in claim 2, wherein the annular magnet comprises a ring inner diameter that is smaller than a diameter of a collar on of the at least one sample vessel, but larger than an outer diameter of a cylindrical region of the at least one sample vessel.

* * * * *